(12) United States Patent
Florent et al.

(10) Patent No.: US 11,980,423 B2
(45) Date of Patent: May 14, 2024

(54) NAVIGATION ASSISTANCE SYSTEM

(71) Applicant: KONINKLIJKE PHILIPS N.V., Eindhoven (NL)

(72) Inventors: Raoul Florent, Ville D'Avray (FR); Pascal Yves François Cathier, Asnières-sur-Seine (FR); Neriman Nicoletta Kahya, Eindhoven (NL); Wilhelmus Henrica Gerarda Maria Van Den Boomen, Valkenswaard (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1569 days.

(21) Appl. No.: 15/779,173

(22) PCT Filed: Dec. 16, 2016

(86) PCT No.: PCT/EP2016/081477
§ 371 (c)(1),
(2) Date: May 25, 2018

(87) PCT Pub. No.: WO2017/103142
PCT Pub. Date: Jun. 22, 2017

(65) Prior Publication Data
US 2018/0353240 A1 Dec. 13, 2018

(30) Foreign Application Priority Data
Dec. 17, 2015 (EP) ..................................... 15307042

(51) Int. Cl.
*A61B 34/10* (2016.01)
*A61B 34/20* (2016.01)
*A61B 90/00* (2016.01)

(52) U.S. Cl.
CPC .............. *A61B 34/10* (2016.02); *A61B 34/20* (2016.02); *A61B 90/39* (2016.02);
(Continued)

(58) Field of Classification Search
CPC ... A61B 34/10; A61B 34/20; A61B 2090/364; A61B 2090/376
See application file for complete search history.

(56) References Cited

U.S. PATENT DOCUMENTS

| | | | | |
|---|---|---|---|---|
| 7,356,367 B2 * | 4/2008 | Liang | ..................... | A61B 90/36 600/407 |
| 2002/0049375 A1 * | 4/2002 | Strommer | ............ | A61B 8/0833 600/407 |

(Continued)

*Primary Examiner* — Anu Ramana

(57) ABSTRACT

The invention relates to a navigation assistance system for assisting in navigating an interventional instrument within a subject. An implanted object opening model (21) and a vessel opening model (27) are generated based on a provided interventional image data set, wherein the models define a respective position, shape and dimension in a frame of reference. These models and a position, which is also provided in the frame of reference, and optionally also a shape (25) of the interventional instrument are used for generating a graphical representation showing the implanted object opening model, the vessel opening model and the provided position and optionally shape of the interventional instrument, thereby providing guidance for a physician, which allows the physician to relatively easily navigate the interventional instrument such that it is moved through the opening of the implanted object and through the opening of the vessel.

13 Claims, 4 Drawing Sheets

(52) U.S. Cl.
CPC ... *A61B 2034/102* (2016.02); *A61B 2034/105* (2016.02); *A61B 2034/2055* (2016.02); *A61B 2034/2061* (2016.02); *A61B 2090/3983* (2016.02)

(56) References Cited

U.S. PATENT DOCUMENTS

| | | |
|---|---|---|
| 2005/0107688 A1* | 5/2005 | Strommer ............ A61B 5/0066 600/424 |
| 2006/0013523 A1 | 1/2006 | Childlers et al. |
| 2006/0058647 A1 | 3/2006 | Strommer |
| 2007/0065077 A1 | 3/2007 | Childers et al. |
| 2008/0285909 A1 | 11/2008 | Younge et al. |
| 2014/0276002 A1 | 9/2014 | West et al. |
| 2016/0081760 A1 | 3/2016 | Verard |
| 2017/0095296 A1 | 4/2017 | Bescos et al. |

* cited by examiner

NAVIGATION ASSISTANCE SYSTEM

CROSS-REFERENCE TO PRIOR APPLICATIONS

This application is the U.S. National Phase application under 35 U.S.C. § 371 of International Application Serial No. PCT/EP2016/081477, filed on Dec. 16, 2016, which claims the benefit of European Patent Application No. 15307042.0, filed on Dec. 17, 2015. This application is hereby incorporated by reference herein.

FIELD OF THE INVENTION

The invention relates to a navigation assistance system, method and computer program for assisting in navigating an interventional instrument within a subject. The invention further relates to an interventional system comprising the navigation assistance system.

BACKGROUND OF THE INVENTION

WO 2014/191262 A3 discloses an assisting apparatus for assisting a user in moving an insertion element to a target element within an object. The assisting apparatus comprises a target element image providing unit for providing a target element image showing the target element and a target element representation generating unit for generating a target element representation representing the target element within the object in its three-dimensional position and three-dimensional orientation and with its size based on the target element image. The target element comprises at least one opening, wherein the target element representation generating unit is adapted to generate a target element representation comprising at least one ring representing the at least one opening of the target element within the object in the three-dimensional position, the three-dimensional orientation and size of the at least one opening of the target element. The assisting apparatus further comprises a tracking unit for tracking a three-dimensional position of the insertion element within the object, while the insertion element is moved to the target element, wherein the tracked insertion element has at least one opening, and a display for displaying the at least one ring of the target element representation and at least one ring representing the at least one opening of the insertion element.

WO 2015/177012 A1 discloses an imaging apparatus for imaging a first object within a second object. The imaging apparatus comprises a representation providing unit for providing a three-dimensional representation of the second object, wherein the three-dimensional representation includes a representation of a surface of the second object. The imaging apparatus further comprises a position providing unit for providing the position of the first object relative to the position of the second object and a projection unit for determining a projection of the first object onto the representation of the surface of the second object based on the provided position of the first object. The projection of the first object on the representation of the surface of the second object is finally displayed.

WO 2014/151651 A1 discloses a navigation assistance system for assisting in navigating an interventional instrument within a patient. The navigation assistance system comprises an electromagnetic tracking system for tracking the position of an interventional instrument like a guidewire or catheter and a memory for storing a patient-specific vessel model representing the geometry of a vessel of the patient. An output generator is used for generating a graphical visualization showing the tracked position of the interventional instrument and the patient-specific vessel model, in order to visualize the spatial relation between the interventional instrument and the vessel. This visualized spatial relation assists a physician in navigating the interventional instrument within the patient.

SUMMARY OF THE INVENTION

It is an object of the present invention to provide a navigation assistance system, method and computer program which allow for an improved assistance in navigating an interventional instrument within a subject. It is a further object of the present invention to provide an interventional system comprising the navigation assistance system.

In a first aspect of the present invention a navigation assistance system for assisting in navigating an interventional instrument within a subject is presented, wherein the navigation assistance system comprises:
  an interventional image data set providing unit for providing an interventional image data set showing an implanted object with an opening and a vessel with an opening,
  a position providing unit for providing the position of the interventional instrument in a frame of reference,
  a model generation unit for generating an implanted object opening model and a vessel opening model based on the provided interventional image data set, wherein the implanted object opening model defines the position, shape and dimension of the opening of the implanted object in the frame of reference and wherein the vessel opening model defines the position, shape and dimension of the opening of the vessel in the frame of reference,
  a graphical representation generation unit for generating a graphical representation of the implanted object opening model, the vessel opening model and the provided position of the interventional instrument.

Since an interventional image data set showing an implanted object with an opening and a vessel with an opening is provided and since this interventional image data set is used for generating the implanted object opening model and the vessel opening model, i.e. since not pre-interventional image data, but intra-operative data, are used for generating the implanted object opening model and the vessel opening model, the implanted object opening model and the vessel opening model accurately represent the position, shape and dimension of the opening of the implanted object and of the opening of the vessel during the interventional procedure. Moreover, since the graphical representation generation unit generates a graphical representation of the implanted object opening model, the vessel opening model and the tracked position of the interventional instrument, the position of the interventional instrument relative to the position, shape and dimension of the opening of the implanted object and relative to the position, shape and dimension of the opening of the vessel can be indicated, while the interventional instrument is navigated within the subject. This provides an improved guidance of a user like a physician, which allows the user to relatively easily navigate the interventional instrument such that it is moved through the opening of the implanted object and through the opening of the vessel.

Preferentially, a position defines a location and optionally also an orientation, i.e., for instance, preferentially the provided position of the interventional instrument defines the location of the interventional instrument, especially of its tip, and optionally also its orientation. The position is preferentially a three-dimensional position.

The position providing unit can be adapted to provide the position of the tip of the interventional instrument only. However, the position providing unit can also be adapted to provide the position of a larger part of the interventional instrument, for instance, the position of the tip and of a part of the interventional instrument being adjacent to the tip. The position providing unit may also be adapted to provide the shape of this larger part such that the graphical representation can also show this shape. The graphical representation may comprise a three-dimensional curve representing the position and shape of this part of the interventional instrument. In an embodiment the position providing unit may provide the position and shape of the entire interventional instrument, wherein the graphical representation may show a three-dimensional curve representing the entire interventional instrument.

The interventional image data set providing unit can be a storing unit in which the interventional image data set is stored, wherein the interventional image data set providing unit can be adapted to provide the stored interventional image data set. The interventional image data set providing unit can also be a receiving unit for receiving the interventional image data set and for providing the received interventional image data set. The interventional image data set providing unit can also be an interventional image data set generation unit for generating the interventional image data set. The interventional image data set preferentially includes interventional two-dimensional x-ray projection images which have been acquired in different acquisition directions and which show the implanted object and the vessel. However, the interventional image data set can also comprise other interventional images showing the implanted object and the vessel like ultrasound images. The interventional image data set preferentially comprises one or several interventional images which have been acquired while a contrast agent was within the vessel, in order to enhance the visibility of the vessel in the interventional image data set. Alternatively or in addition, the interventional image data set may comprise one or several images showing the implanted object and the vessel without a contrast agent.

The model generation unit can be adapted to segment the vessel, which may be regarded as being a first vessel, and optionally one or several further vessels, and the implanted object, i.e., for instance, at least markers of the implanted object surrounding the opening of the implanted object, in the interventional image data set and to use these segmentations for generating the vessel opening model and the implanted object opening model.

The opening of the vessel is preferentially an ostium of the vessel. The implanted object is preferentially a fenestrated stent, wherein the opening is preferentially a fenestration of the stent, which should be aligned with the ostium of the vessel, wherein the navigation assistance system is preferentially adapted to assist the user in navigating the interventional instrument through the fenestration of the fenestrated stent, which may also be regarded as being a gate, and through the ostium into the vessel. The interventional instrument may be a catheter, a wire like a guidewire, a needle or another interventional instrument.

The position providing unit can be adapted to receive the position of the interventional instrument from a tracking unit for tracking the position of the interventional instrument and to provide the received position of the interventional instrument. However, the position providing unit can also be the tracking unit itself. In an embodiment the position providing unit is a tracking unit for tracking the position of the interventional instrument by optical shape sensing. However, the position of the interventional instrument can also be tracked by using another tracking technique like electromagnetic tracking. The position providing unit is preferentially adapted to provide the position of the interventional instrument in real-time, while the interventional instrument is moved, i.e. the position providing unit is preferentially adapted to provide the real-time position of the interventional instrument.

The tracked position of the interventional instrument and the interventional image data set are registered to each other such that the spatial relationship between the generated implanted object opening model, the generated vessel opening model and the tracked position of the interventional instrument is known and can be provided in the same frame of reference. For instance, an interventional image data set generation unit generating the interventional image data set like an x-ray C-arm system and a tracking unit like an optical shape sensing tracking unit can be registered to each other such that the interventional image data set generated by the interventional image data set generation unit and the position of the interventional instrument tracked by the tracking unit are registered to each other.

In an embodiment the model generation unit is adapted to use the provided position of the interventional instrument for generating the implanted object opening model and/or for generating the vessel opening model. For instance, if the model generation unit is adapted to generate the vessel opening model based on a segmentation of one or several vessels in two-dimensional x-ray projection images, the application of a corresponding segmentation algorithm may be confined to a region surrounding a virtual projection of the provided position of the interventional instrument onto an imaging plane of the respective two-dimensional x-ray projection image, thereby allowing for a faster and maybe more accurate segmentation of the desired structure. Also a segmentation of the opening of the implanted object, for instance, by segmenting markers surrounding the opening of the implanted object, can be confined to a region surrounding the virtual projection of the provided position of the interventional instrument, in order to facilitate the segmentation of the opening of the implanted object.

The interventional image data set providing unit can be adapted to provide the interventional image data set such that it comprises at least one first interventional image showing the implanted object and the vessel without a contrast agent and at least one second interventional image showing the implanted object and the vessel with a contrast agent, wherein the model generation unit is adapted to generate the implanted object opening model based on the at least one first interventional image and to generate the vessel opening model based on the at least one second interventional image. The generation of the implanted object opening model is therefore not disturbed by a contrast agent, thereby allowing for an improved generation of the implanted object opening model. Moreover, since the vessel opening model is determined based on the at least one second interventional image showing the vessel with a contrast agent, the vessel opening model can be more reliably determined. Preferentially at least a pair of two-dimensional x-ray projection images without a contrast agent is used as first interventional images and at least a further pair of two-dimensional x-ray projection images with a contrast agent is used as second interventional images.

The implanted object preferentially comprises markers having a known spatial relation to the opening of the implanted object, wherein the interventional image data set providing unit is adapted to provide the interventional image data set such that it shows the markers of the implanted object, wherein the model generation unit is adapted to detect the positions of the markers in the interventional image data set and to generate the implanted object opening model based on the detected positions of the markers and the known spatial relation. The implanted object can comprise several markers surrounding the opening of the implanted object such that by detecting the markers in the interventional image data set the opening can be detected, wherein this detection can be used for generating the implanted object opening model. In particular, the model generation unit can be adapted to determine two-dimensional positions of the markers in two-dimensional x-ray projection images, to determine three-dimensional positions of the markers based on the determined two-dimensional positions and the so called epipolar geometry and to fit a circle or another shape, which corresponds to the shape of the opening of the implanted object, to the determined three-dimensional marker positions, in order to generate the implanted object model.

The model generation unit may be adapted to determine the position of at least a part of the implanted object in the interventional image data set, to generate the implanted object opening model by using the determined position of at least the part of the implanted object, to determine the position, dimensions and shape of at least a part of the vessel in the interventional image data set by using the determined position of at least the part of the implanted object and to generate the vessel opening model based on the determined position, dimension and shape of at least the part of the vessel in the image data set. For instance, if positions of markers surrounding the opening of the implanted object have been determined already in a two-dimensional x-ray projection image, a segmentation of at least a part of the vessel for determining its position, dimensions and shape in the two-dimensional x-ray projection image can be confined to region surrounding the determined positions of the markers. Also this can facilitate the generation of the vessel opening model.

The navigation assistance system preferentially further comprises a path determination unit for determining a path along which the interventional instrument is movable for moving the interventional instrument through the opening of the implanted object and through the opening of the vessel, wherein the path determination unit is adapted to determine the path based on the generated implanted object opening model, the generated vessel opening model and the provided position of the interventional instrument, wherein the graphical representation generation unit is adapted to generate the graphical representation such that it also includes the determined path. By also representing the path along which the interventional instrument is movable for moving the interventional instrument through the opening of the implanted object and through the opening of the vessel the guidance of the user while navigating the interventional instrument within the subject can be further improved. The path determination unit can be adapted to determine the path by defining a line starting from the provided position of the interventional instrument and traversing the two openings of the implanted object and the vessel, especially traversing as good as possible the centers of these openings. The path determination unit can be adapted to use fitting algorithms for determining the path, wherein constraints can be used like a maximum degree of curvature of the interventional instrument which cannot be exceeded.

In an embodiment the interventional image data set providing unit is adapted to provide the interventional image data set such that it shows the vessel with the opening, which is regarded as being a first vessel, and a second vessel, wherein the first vessel and the second vessel are connected via the opening and wherein the model generation unit is adapted to generate a first vessel model defining the position, shape and dimensions of the first vessel, to generate a second vessel model defining the position, shape and dimensions of the second vessel and to generate the vessel opening model based on the generated first vessel model and the generated second vessel model. This can allow for an accurate generation of the vessel opening model based on segmentations of the first and second vessels in the interventional image data set. The implanted object may be implanted in the second vessel, wherein the opening of the implanted objected is aligned with the opening of the first vessel, which provides a fluid connection between the first and second vessels. The graphical representation of the implanted object opening model, the vessel opening model and the provided position of the interventional instrument then provides assistance for navigating the interventional instrument from the second vessel through the opening of the implanted objected and through the opening of the first vessel into the first vessel. For instance, it provides assistance for navigating the interventional instrument from the second vessel through a fenestration of a stent, which may be implanted in the second vessel, and through an ostium of the first vessel into the first vessel.

In an embodiment the graphical representation generation unit is adapted to generate the graphical representation in accordance with representation parameters defining how the implanted object opening model, the vessel opening model and the provided position of the interventional instrument are to be presented, wherein the representation parameters depend on the provided position of the interventional instrument. For instance, the representation parameters can define the size of the graphical representation and hence the magnification and/or the viewing direction. In particular, the representation parameters can define whether the graphical representation should represent the different elements in a lateral view, in which the position of the interventional instrument and the opening models are shown from aside, or in a so called bull's eye view in which the opening models are in a viewing plane and the position of the interventional instrument is seen from the top. The representation parameters can depend on the distance between a) the position of the interventional instrument and b) the position of the opening of the implanted object and/or the position of the opening of the vessel. For example, if this distance is larger, the size of the different elements may be smaller, i.e. the magnification may be smaller, and, if this distance is smaller, the size of the different elements may be larger, i.e. the magnification may be larger. Moreover, if this distance is larger, the lateral view may be shown, and, if this distance is smaller, the bull's eye view may be shown. It is also possible that the lateral view is always shown and that the bull's eye view is shown only, if the distance is smaller than a predefined or selectable threshold. Furthermore, in an embodiment both views or multiple other views may be shown independently of the position of the interventional instrument and only the magnification may be modified depending on the distance.

In a further aspect of the present invention an interventional system for performing an interventional procedure is presented, wherein the interventional system comprises:
an interventional instrument,
a navigation assistance system for assisting in navigating the interventional instrument as defined in claim 1.

In another aspect of the present invention a navigation assistance method for assisting in navigating an interventional instrument within a subject is presented, wherein the navigation assistance method comprises:
providing an interventional image data set showing an implanted object with an opening and a vessel with an opening by an interventional image data set providing unit,
providing the position of the interventional instrument by a position providing unit in a frame of reference,
generating an implanted object opening model and a vessel opening model based on the provided interventional image data set by a model generation unit, wherein the implanted object opening model defines the position, shape and dimension of the opening of the implanted object in the frame of reference and wherein the vessel opening model defines the position, shape and dimension of the opening of the vessel in the frame of reference,
generating a graphical representation of the implanted object opening model, the vessel opening model and the provided position of the interventional instrument by a graphical representation generation unit.

In a further preferred aspect of the present invention a computer program for assisting in navigating an interventional instrument is presented, wherein the computer program comprises program code means for causing a navigation assistance system as defined in claim 1 to carry out the navigation assistance method as defined in claim 13, when the computer program is run on the navigation assistance system.

It shall be understood that the navigation assistance system of claim 1, the interventional system of claim 12, the navigation assistance method of claim 13 and the computer program of claim 14 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings.

DETAILED DESCRIPTION OF EMBODIMENTS

Figure 1:
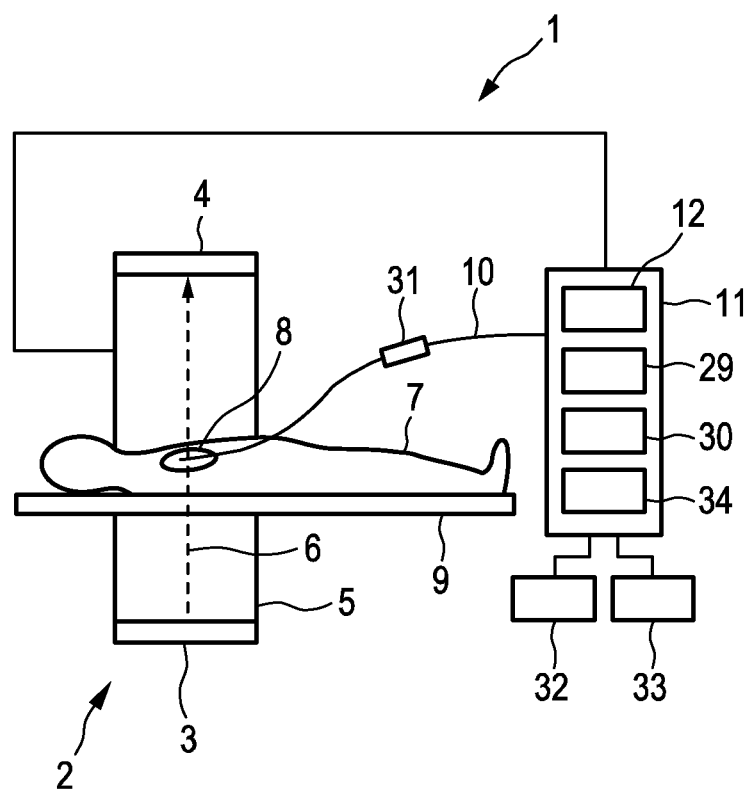
FIG. 1 shows schematically and exemplarily an embodiment of an interventional system for performing an interventional procedure.

FIG. 1 shows schematically and exemplarily an embodiment of an interventional system for performing an interventional procedure. The interventional system 1 comprises an interventional instrument 10 like a catheter or guidewire for being navigated within a patient 7 arranged on a support means like a table 9. The interventional instrument 10 can comprise a handle 31 allowing a physician to navigate the interventional instrument 10 within the patient 7, especially within the heart 8 of the patient 7. The handle 31 can be adapted to allow the physician to push and pull the interventional instrument 10 and to deflect the distal tip of the interventional instrument 10. The handle 31 can particularly be used for moving the distal tip of the interventional instrument 10 through an opening of a fenestrated stent, which has been implanted in a vessel, and through an ostium of a further vessel, in order to navigate the distal tip of the interventional instrument 10 into the further vessel. In the following the further vessel is denoted as first vessel and the vessel, in which the fenestrated stent is implanted, is denoted as second vessel.

The interventional system 1 further comprises an interventional image data set providing unit 2 for providing an interventional image data set showing the fenestrated stent and at least the first vessel. In this embodiment the interventional image data set providing unit 2 is an x-ray C-arm system for acquiring two-dimensional x-ray projection images in different acquisition directions. The x-ray C-arm system comprises an x-ray source 3 for emitting x-rays 6 and a detector 4 for detecting the x-rays 6 after having traversed the patient 7 and for generating a two-dimensional x-ray projection image based on the detected x-rays 6. The x-ray source 3 and the detector 4 are arranged at opposing ends of a C-arm 5 which is rotatable around the patient 7, in order to provide two-dimensional x-ray projection images in different acquisition directions, which are provided to a control and processing device 11. Preferentially, a contrast agent is injected at least into the first vessel, in order to enhance the detectability of at least the first vessel in the two-dimensional x-ray projection images.

The interventional system 1 further comprises a model generation unit 29 for generating an implanted object opening model, i.e. a model of the fenestration of the fenestrated stent, based on the provided interventional image data set, wherein the implanted object opening model defines the position, shape and dimension of the opening of the implanted object in a frame of reference. Preferentially the fenestrated stent comprises markers surrounding the opening of the fenestrated stent, wherein the markers are adapted to be relatively easily detectable in a two-dimensional x-ray projection image. For instance, three or more markers, which are preferentially metallic, are arranged around the opening of the fenestrated stent. The markers are preferentially equidistantly distributed around the opening of the fenestrated stent.

The model generation unit 29 can be adapted to detect the markers surrounding the opening, i.e. surrounding the fenestration, of the fenestrated stent in different two-dimensional x-ray projection images, which have been acquired in different acquisition directions, thereby determining two-dimensional positions of the markers in the different two-dimensional x-ray projection images. These two-dimensional positions of the markers can be used by the model generation unit 29 for determining the three-dimensional positions of the markers by using known localization techniques which may be based on, for instance, an intersection of rays defined by the respective two-dimensional position of the respective marker in the respective two-dimensional x-ray projection image and the respective position of the x-ray source. After the three-dimensional positions of the markers have been determined, a circle or, if the fenestration has another shape, another object can be fitted to the three-dimensional positions of the markers, in order to generate the implanted object opening model. The implanted object opening model can have a predefined or selectable appearance, i.e. for example, having a predefined or selectable line width and/or color.

In another embodiment the model generation unit 29 may be adapted to generate the implanted object opening model in another way. For instance, instead of using markers surrounding the opening of the fenestrated stent a segmentation algorithm may be used, which is adapted to directly segment the opening of the fenestrated stent in the two-dimensional x-ray projection images, in order to determine the two-dimensional dimensions and positions of the opening of the fenestrated stent in the respective two-dimensional x-ray projection images, wherein also these two-dimensional dimensions and positions of the opening of the fenestrated stent in the different two-dimensional x-ray projection images can be used for generating the implanted object opening model 21.

In particular, for determining a three-dimensional position of an element like a marker a pair of two-dimensional x-ray projection images and optionally one or more further two-dimensional x-ray projection images are used, wherein each of these two-dimensional x-ray projection images shows a projection of the element. The two-dimensional x-ray projection images of the pair have been acquired in different acquisition directions, wherein the angular difference between these acquisition directions is preferentially at least 30 degrees. In each two-dimensional x-ray projection image the position of the element, i.e. of the projection of the element, is identified and these positions are used together with the known acquisition geometry for defining for each two-dimensional x-projection image a corresponding projection line in three dimensions, on which the respective element projection is located. The intersection of these projection lines defines the three-dimensional position of the element. If the projection lines do not intersect, for instance, because of an inaccuracy in the data defining the acquisition geometry or because of patient motion between the acquisitions of the different two-dimensional x-ray projection images, the three-dimensional position being closest to the projection lines can be determined as defining the three-dimensional position of the element. For detecting the element in the two-dimensional x-ray projection images known detection techniques can be used. In an embodiment the element is detected in one of the two-dimensional x-ray projection images, wherein the detected element in the projection image is used together with the acquisition geometry for defining a corresponding projection line in three dimensions. In the other of the pair of two-dimensional x-ray projection images the counterpart projection of the element can be detected by using a pairing operation, wherein this pairing operation can be realized by using the epipolar geometry and by resorting to a similarity criterion. The two-dimensional x-ray projection images can be used for determining the three-dimensional positions of the markers. However, they can of course also be used for determining three-dimensional positions of other elements like a branching point between two vessels, which may be detected in the two-dimensional x-ray projection images. In this way the three-dimensional position of the ostium of a vessel can be determined.

For generating the implanted object opening model 21 interventional images may be used, which have been acquired after a contrast agent has been injected, and/or interventional images may be used, which have been acquired without having injected a contrast agent. In the latter case the detectability of the opening of the fenestrated stent, especially of the markers surrounding the opening of the fenestrated stent, may be improved, because there may be less disturbance by the contrast agent.

The model generation 29 is further adapted to generate a model of the opening of the first vessel, i.e. of the ostium of the first vessel, based on the provided interventional image data set. For generating this vessel opening model the model generation unit 29 preferentially uses two-dimensional x-ray projection images which have been generated in different acquisition directions, after a contrast agent has been injected such that it is present in the first and second vessels. The model generation unit 29 is preferentially adapted to segment the first and second vessels in the different two-dimensional x-ray projection images, in order to determine the two-dimensional dimensions and positions of the first and second vessels in the respective two-dimensional x-ray projection images, wherein these determined two-dimensional dimensions and positions in the different two-dimensional x-ray projection images can be used for determining the three-dimensional dimensions and positions of the first and second vessels by using known techniques which may be based, for instance, on intersections between rays defined by respective two-dimensional dimensions and positions in respective two-dimensional x-ray projection images and by respective three-dimensional positions of the x-ray source. The model generation unit 29 may be further adapted to determine the connection area where the first and second vessels are connected, wherein the circumference of the connection area can define the three-dimensional vessel opening model. In other embodiments other techniques can be used for generating the model of the ostium of the first vessel based on the provided interventional image data set. For instance, the ostium may directly be segmented in the two-dimensional x-ray projection images, in order to determine the two-dimensional dimensions and positions of the ostium in the two-dimensional x-ray projection images, and the three-dimensional model of the ostium may be determined based on the determined two-dimensional dimensions and positions by using known techniques which may be based, for instance, on intersections between rays defined by respective two-dimensional dimensions and positions in respective two-dimensional x-ray projection images and by respective three-dimensional positions of the x-ray source.

The model generation unit 29 is adapted to generate the vessel opening model such that it models at least the ostium of the first vessel and preferentially also an adjacent part of the first vessel. The adjacent part of the first vessel, i.e. the part of the first vessel being adjacent to the ostium, can be determined based on the two-dimensional dimension and position of the first vessel detected in the respective two-dimensional x-ray projection images and the epipolar geometry.

The interventional system 1 further comprises a position providing unit 12 for providing the position of the interventional instrument 10. In this embodiment the interventional instrument 10 is enabled to allow for a determination of the position of the interventional instrument 10 by optical shape sensing. In particular, the interventional instrument 10 comprises optical fibers with Bragg gratings and the position providing unit 12 comprises a light source and a light detector for emitting light into the optical fibers and for detecting light received from the optical fibers, wherein the detected light is used for determining the three-dimensional shape of the interventional instrument 10 and three-dimensional position of this shape. The optical shape sensing technology has been described in U.S. Patent Application Publications 2006/0013523 A1 and 2007/0065077 A1 and has been proposed for integration into medical instruments (e.g., guidewires and catheters) in U.S. Patent Application Publication US 2008/0285909 A1. The optical shape sensing technique is sometimes called FORS (Fiber-Optic RealShape) technique.

The model generation unit 29 can be adapted to use the known position of the interventional instrument 10 for generating the model of the fenestration of the fenestrated stent and/or the model of the ostium of the first vessel. A user may indicate via an input unit 32, when the generation of the model of the fenestration and/or of the model of the ostium should start, wherein the user may provide this indication, when the tip of the interventional instrument is close to the openings as recognizable by the user based on, for example, a two-dimensional x-ray projection image showing the tip and the markers surrounding the fenestration. In particular, if the user has indicated that the modeling process should be started and if the model generation unit 29 is adapted to generate the vessel opening model based on a segmentation of one or several vessels in two-dimensional x-ray projection images, the application of a corresponding segmentation algorithm may be confined to a region surrounding a virtual projection of the provided position of the interventional instrument onto an imaging plane of the respective two-dimensional x-ray projection image, thereby allowing for a faster and maybe more accurate segmentation of the desired structure. Also a segmentation of the opening of the implanted object, for instance, by segmenting markers surrounding the opening of the implanted object, can be confined to a region surrounding the virtual projection of the provided position of the interventional instrument. The region surrounding the virtual projection of the provide position of the interventional instrument can have a predefined or selectable diameter, wherein this region may be circular or spherical and the known projected position of the interventional instrument, especially of its distal tip, may be in the center of this region. Moreover, if positions of markers surrounding the opening of the implanted object have been determined already in a two-dimensional x-ray projection image, a segmentation of at least a part of the vessel for determining its position, dimensions and shape in the two-dimensional x-ray projection image can be confined to a region surrounding the determined positions of the markers.

The model generation unit 29 is preferentially adapted to use only interventional, i.e. intra-operative, image data, but no pre-interventional image data for generating the models.

The interventional image data set providing unit 2 and the position providing unit 12, i.e. the x-ray C-arm system and the optical shape sensing tracking system, are registered to each other by using known registration techniques such that the position of the interventional instrument 10 as provided by the position providing unit 12 is known relative to a coordinate system defined by the interventional image data set providing unit 2.

The interventional image data set providing unit 2 can be adapted to provide the interventional image data set such that it comprises first interventional images showing the fenestrated stent without a contrast agent and second interventional images showing the fenestrated stent and the first and second vessels with a contrast agent, wherein the model generation unit 29 may be adapted to generate the model of the fenestration of the fenestrated stent based on the first interventional images and to generate the model of the ostium of the first vessel based on the second interventional images, wherein the first interventional images and the second interventional images are registered to each other by being acquired by using the same interventional image data set providing unit 2.

The interventional system 1 further comprises a path determination unit 30 for determining a path along which the interventional instrument 10 is movable for moving the interventional instrument 10 through the fenestration of the fenestrated stent and through the ostium of the first vessel, wherein the path determination unit 30 is adapted to determine the path based on the generated model of the fenestration of the fenestrated stent, the generated model of the ostium of the first vessel and the provided position of the interventional instrument 10.

Figure 2:
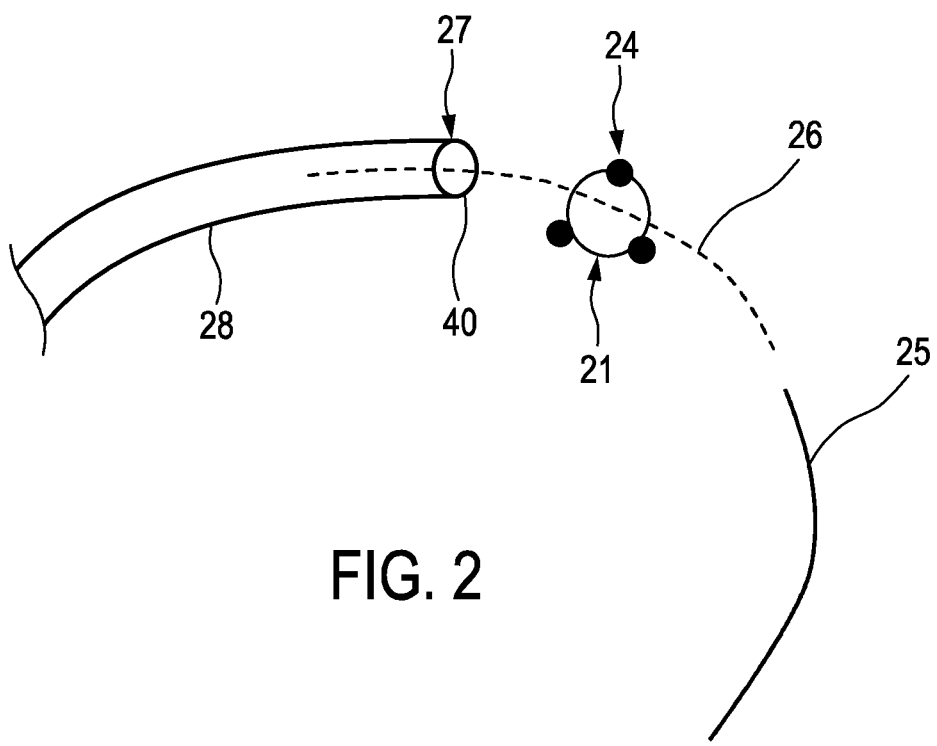
FIG. 2 shows schematically and exemplarily a visualization of a vessel, of an opening of a fenestrated stent, of a distal end of an interventional instrument and of a path along which the interventional instrument may be moved.

The interventional system 1 further comprises a graphical representation generation unit 34 for generating a graphical representation including the implanted object opening model 21, the vessel opening model 27 showing the vessel opening 40, i.e. the ostium, and the adjacent part 28, the provided position and shape 25 of the distal end of the interventional instrument and the determined path 26. The graphical representation can optionally further include the markers 24 as schematically and exemplarily shown in FIG. 2. The graphical representation can be displayed on a display 33.

The input unit 32 allows a user to input data, information, indications et cetera into the interventional system 1. For instance, the input 32 may be used for allowing the user to indicate when an interventional image data set to be used for the generation of the models should be acquired. The user may provide this indication when the distal end of the interventional instrument is close to the fenestration of the stent and/or close to the ostium of the first vessel. It may also be used to allow the user to indicate that the navigation assistance, i.e. the generation and displaying of the graphical representation, should start or stop. The input unit 32 may comprise, for instance, a keyboard, a computer mouse, a touch pad, a foot switch, a button to be actuated by hand, et cetera.

Since the interventional image data set providing unit, the position providing unit, the model generation unit, the graphical representation generation unit and the path determination unit are adapted to finally provide a representation of the spatial relationships between the ostium of the first vessel, the fenestration of the fenestrated stent and the current, real-time position of the distal end of the interventional instrument and also a representation of an optimal path, these components can be regarded as being components of a navigation assistance system for assisting in navigating the interventional instrument within the patient.

Figure 3:
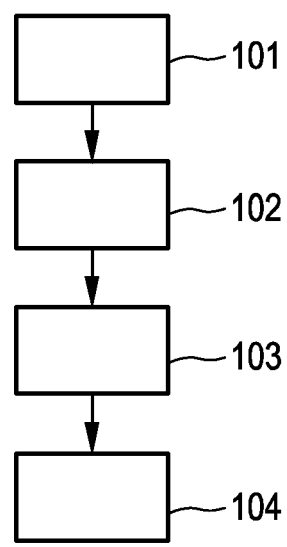
FIG. 3 shows a flowchart exemplarily illustrating an embodiment of a navigation assistance method for assisting in navigating an interventional instrument within a subject.

In the following an embodiment of a navigation assistance method for assisting in navigating an interventional instrument within a subject will exemplarily be described with reference to a flowchart shown in FIG. 3.

In step 101 the interventional instrument 10 is introduced into the patient 7 and moved such that the distal tip of the interventional instrument 10 is close to the fenestration of the fenestrated stent and/or to the ostium of the first vessel. During this movement the interventional image data set providing unit 2 can provide interventional images, especially two-dimensional x-ray projection images, which can be shown on the display 33, in order to provide some guidance for the physician navigating the interventional instrument 10.

After the distal tip of the interventional instrument 10 has been moved to be close to the fenestration of the fenestrated stent and/or close to the ostium of the first vessel, in step 102 the interventional image data set providing unit 2 provides an interventional image data set showing at least the first vessel and the fenestrated stent. The interventional image data set can comprise contrast agent images, in order to allow for a simplified detection of the first vessel in the interventional image data set.

In step 103 the provided interventional image data set is used by the model generation unit 29 for generating an implanted object opening model and for generating a vessel opening model based on the interventional image data set. In addition, the path determination unit 30 determines a path along which the interventional instrument 10 is movable for moving the interventional instrument 10 through the fenestration of the fenestrated stent and through the ostium of the first vessel based on the generated implanted opening model, the generated vessel opening model and the current position of the interventional instrument 10.

In step 104 a graphical representation is generated and displayed, wherein the graphical representation comprises the vessel opening model, the implanted object opening model, the determined path and the current position of the interventional instrument, in order to visualize their spatial relationship. Preferentially, the position of the interventional instrument 10 and the determination of the path, which considers, inter alia, the current position of the interventional instrument 10, are continuously updated, wherein the updated position of the interventional instrument 10 and the updated path are shown together with the models determined in step 103 on the display 33, in order to allow the physician to monitor the movement of the interventional instrument 10 and to always show an optimal path considering the current, real-time position of the interventional instrument 10.

In an embodiment the graphical representation generation unit 34 is adapted to generate the graphical representation in accordance with representation parameters defining how the implanted object opening model 21, the vessel opening model 27, the determined path 26 and the provided position and shape 25 of the interventional instrument 10 are to be presented, wherein the representation parameters depend on the provided position of the interventional instrument. For instance, the representation parameters can define the size of the graphical representation and hence the magnification and/or the viewing direction. In particular, the representation parameters can define whether the graphical representation should represent the different elements in a lateral view or in a bull's eye view. The representation parameters can depend on the distance between a) the position of the interventional instrument and b) the position of the opening of the implanted object and/or the position of the opening of the vessel. For example, if this distance is larger, the size of the different elements may be smaller, i.e. the magnification may be smaller, and, if this distance is smaller, the size of the different elements may be larger, i.e. the magnification may be larger. Moreover, if this distance is larger, the lateral view may be shown, and, if this distance is smaller, the bull's eye view may be shown. It is also possible that the lateral view is always shown and that the bull's eye view is shown only, if the distance is smaller than a predefined or selectable threshold. Furthermore, in an embodiment both views or multiple other views may be shown independently of the position of the interventional instrument and only the magnification may be modified depending on the distance.

The interventional system can be adapted to be used in an EVAR procedure. During this EVAR procedure a fenestrated stent may be implanted in the aorta such that fenestrations of the stent are aligned with ostia of branching arteries. After the fenestrated stent has been implanted in the aorta such that the fenestrations are aligned with the ostia of the branching arteries, it may be required to navigate an interventional instrument through a fenestration of the implanted stent and through an ostium into a branching artery, wherein the alignment between the fenestration of the implanted stent, which may also be regarded as being a gate, and the ostium may not necessary be well aligned.

Figure 4:
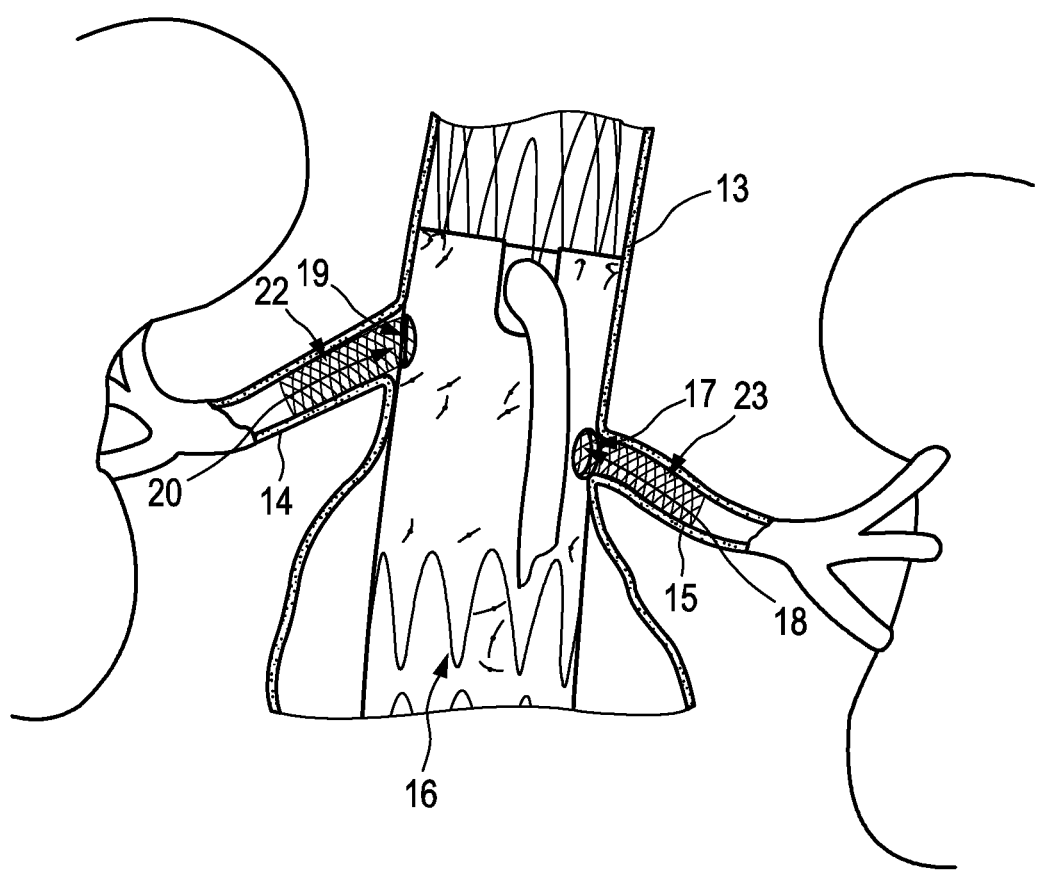
FIG. 4 illustrates schematically and exemplarily an endovascular aneurysm repair (EVAR) procedure.

In the case of a suprarenal aneurysm a fenestrated stent may be implanted such that the openings, i.e. the fenestrations, of the stent are at least roughly located in front of the renal ostia as schematically and exemplarily illustrated in FIG. 4. In particular, FIG. 4 shows a stent graft 16 with openings 18, 19 aligned with renal ostia 17, 20 of renal arteries 14, 15 branching from the aorta 13. In order to complete the treatment of the endovascular aneurysm, also the renal arteries 14, 15 may need to be stented by using stents 22, 23. For stenting a renal artery 14, which may be regarded as being a first vessel, a wire, which has been inserted in the aorta 13, may be threaded into the renal artery 14. This threading requires a steering through the double difficulty constituted by the gate, i.e. the fenestration 19, and the renal ostium 20. Generally, such a steering may be achieved under the guidance of two-dimensional x-ray projection images showing at least the gate. However, finding the three-dimensional path through the gate and the possibly misaligned arterial ostium based on the two-dimensional x-ray projection image is very difficult. In order to facilitate that complex simultaneous gate and ostium wiring, the navigation assistance system creates the virtual navigation view, i.e. the graphical representation, containing at least the three main elements being a modeling of the fenestration complex, i.e. a modeling of the gate which may be regarded as being an implanted object opening model, a modeling of the targeted vessel, i.e. of the anatomy of the targeted vessel which includes at least the ostium and which may therefore also be regarded as being a vessel opening model, and a live-tracked position of the threaded system, i.e. of the wire being in this example the interventional instrument, wherein, for instance, a curve or silhouette representing the tip of the wire and a part adjacent to the tip may be shown. Preferentially, modeling of both the gate and the anatomy occurs at a very late stage, i.e. just prior gate passing, such that the dimension and position of the gate and of the ostium and optionally also of further parts of the renal artery can be determined very accurately, especially because the motion caused by the deployment of the already implemented stent, which may also be regarded as being a stent main body, is already considered. Since the wire is tracked in real-time by using, for instance, optical shape sensing, the virtual navigation view constitutes an exceptionally useful and precise steering facility.

The interventional image data set providing unit can be adapted to provide an interventional image data set comprising at least two angiograms which show the renal arteries, the aorta and the implanted stent prior to fenestration wiring, wherein the at least two angiograms are preferentially acquired under distinct angulations, i.e. in different acquisition directions. The provided interventional image data set may comprise angiograms which are contrast-agent free and angiograms which have been acquired while a contrast agent was present in the patient to be examined. The contrast agent may be injected in a super-selective way, in order to limit the impact of the contrast agent, i.e. the contrast agent may be injected in a vessel-targeted way. For instance, the respective side branch, i.e. the respective artery, can be targeted and selectively injected. In particular, the renal and the internal iliac arteries may be targeted and selectively injected. The position providing unit can be adapted to provide a live localization of the wire to be used for stenting also the renal arteries. Thus, the position providing unit can be adapted to provide an accurate live three-dimensional wire tracking, wherein preferentially optical shape sensing is used, in order to integrate a curve representing a distal part of the wire in the virtual view. If in another embodiment another tracking technique is used like electromagnetic tracking, wherein only the tip of the wire may be tracked, only the position of the tip of the wire may be integrated in the virtual view.

In order to perform the super-selective injection of the contrast agent, a catheter may be used, which is equipped with optical shape sensing technology, in order to allow for a determination of the position and shape of the catheter by optical shape sensing.

The model generation unit is adapted to generate the implanted object opening model, wherein this generation of this model may also be regarded as being a gate modeling. In an embodiment this gate modeling is achieved from the gate markers, i.e. the markers surrounding the respective fenestration, detected under both angulation and classical modeling. However, this gate modeling is preferentially only started when the localized device, i.e. the interventional instrument, is situated close to the gate. This can facilitate the distinction of the gate markers from cluttered material which may be produced by the rest of the stent-body. It is also possible to start marker detection in images without a contrast agent and to propagate this detection to images which have been acquired by using a contrast agent. Another alternative is to rely on the injection of the contrast agent to localize the gate markers. In particular, if a catheter equipped with optical shape sensing technology is used for super-selectively injecting the contrast agent in a targeted vessel, the position of the catheter can be used for defining a region of interest in the images, in which the marker detection should be performed. The catheter can also directly be detected in the respective image by using corresponding segmentation algorithms, in order to define a region in the images in which the marker detection should be performed. This region can also manually be indicated by a user on the respective image which is preferentially an x-ray projection image. This region, which may be regarded as being a region of interest or a confining region and to which the marker detection may be confined, may also be determined by using the position of the wire to be used for stenting the renal arteries.

The model generation unit can perform a vessel modeling, i.e. it can generate the vessel opening model which in this case also represents a part of the vessel adjacent to the opening. The vessel modeling may be performed by using vessel segmentation in at least two views, i.e. in at least two two-dimensional x-ray projection images which have been acquired in two acquisition directions, and by using a classical modeling technique, i.e., for instance, by using the epipolar geometry. Since only the ostium and the ostium segment are modeled, the pairing of the two vessels connected via the ostium may be tracked. The ostium itself is a good anchor point for pairing. Again the presence of the nearby localized device, for instance, of the localized wire or the localized catheter used for super-selective injection, can be used to facilitate local vessel segmentation in the images. Alternatively or in addition, it is also possible to rely on previous gate detection.

In order to create a visual navigation view, the live device localization, i.e. the live provision of the position of the interventional instrument which might be, for instance, a catheter, a guidewire, et cetera, can be merged with the modeled gate and the modeled vessel. The resulting three-dimensional information about the gate, the vessel including the ostium and the interventional instrument can be used to compute an optimal path for optimal threading.

The interventional system may be applied in interventional suites, hybrid rooms and catheter labs with x-ray systems.

The position of the interventional instrument is preferentially shown on the display without using a model modeling the interventional instrument. The curve provided by optical shape sensing may directly be shown on the display.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

Procedures like the provision of the interventional image data set, the provision of the position of the interventional instrument, the generation of models, the determination of a path, et cetera performed by one or several units or devices can be performed by any other number of units or devices. These procedures and/or the control of the navigation assistance system in accordance with the navigation assistance method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a navigation assistance system for assisting in navigating an interventional instrument within a subject. An implanted object opening model and a vessel opening model are generated based on a provided interventional image data set, wherein the models define a respective position, shape and dimension in a frame of reference. These models and a position, which is also provided in the frame of reference, and optionally also a shape of the interventional instrument are used for generating a graphical representation showing the implanted object opening model, the vessel opening model and the provided position and optionally shape of the interventional instrument, thereby providing guidance for a physician, which allows the physician to relatively easily navigate the interventional instrument such that it is moved through the opening of the implanted object and through the opening of the vessel.

The invention claimed is:

1. A navigation assistance system for assisting in navigating an interventional instrument within a subject, the navigation assistance system comprising:
an interventional image data set providing unit configured to provide an interventional image data set showing an implanted object with an opening and a vessel with an opening,
a position providing unit configured to provide a position of the interventional instrument in a frame of reference,
a model generation unit configured to generate an implanted object opening model and a vessel opening model based on the provided interventional image data set, wherein the implanted object opening model defines a position, shape and dimension of the opening of the implanted object in the frame of reference and wherein the vessel opening model defines a position, shape and dimension of the opening of the vessel in the frame of reference,
a graphical representation generation unit configured to generate a graphical representation of the implanted object opening model, the vessel opening model and the provided position of the interventional instrument.

2. The navigation assistance system as defined in claim 1, wherein the position providing unit is adapted to provide the position of the interventional instrument in real-time, while the interventional instrument is moved.

3. The navigation assistance system as defined in claim 1, wherein the position providing unit is adapted to provide the position of the interventional instrument by optical shape sensing.

4. The navigation assistance system as defined in claim 1, wherein the interventional image data set providing unit is adapted to provide the interventional image data set such that it comprises two-dimensional x-ray projection images which have been acquired in different acquisition directions and which show the implanted object and the vessel.

5. The navigation assistance system as defined in claim 1, wherein the model generation unit is adapted to use the provided position of the interventional instrument for generating the implanted object opening model and/or for generating the vessel opening model.

6. The navigation assistance system as defined in claim 1, wherein the interventional image data set providing unit is adapted to provide the interventional image data set such that it comprises at least one first interventional image showing the implanted object and the vessel without a contrast agent and at least one second interventional image showing the implanted object and the vessel with a contrast agent, wherein the model generation unit is adapted to generate the implanted object opening model based on the at least one first interventional image and to generate the vessel opening model based on the at least one second interventional image.

7. The navigation assistance system as defined in claim 1, wherein the implanted object comprises markers having a known spatial relation to the opening of the implanted object, wherein the interventional image data set providing unit is adapted to provide the interventional image data set such that it shows the markers of the implanted object, wherein the model generation unit is adapted to detect positions of the markers in the interventional image data set and to generate the implanted object opening model based on the detected positions of the markers and the known spatial relation.

8. The navigation assistance system as defined in claim 1, wherein the model generation unit is adapted to determine a position of at least a part of the implanted object in the interventional image data set, to generate the implanted object opening model by using the determined position of at least the part of the implanted object, to determine a position, dimension and shape of at least a part of the vessel in the interventional image data set by using the determined position of at least the part of the implanted object and to generate the vessel opening model based on the determined position, dimension and shape of at least the part of the vessel in the image data set.

9. The navigation assistance system as defined in claim 1, wherein the navigation assistance system further comprises a path determination unit configured to determine a path along which the interventional instrument is movable for moving the interventional instrument through the opening of the implanted object and through the opening of the vessel, wherein the path determination unit is adapted to determine the path based on the generated implanted object opening model, the generated vessel opening model and the provided position of the interventional instrument, wherein the graphical representation generation unit is adapted to generate the graphical representation such that it also includes the determined path.

10. The navigation assistance system as defined in claim 1, wherein the interventional image data set providing unit is adapted to provide the interventional image data set such that it shows the vessel with the opening, which is a first vessel, and a second vessel, wherein the first vessel and the second vessel are connected via the opening, wherein the model generation unit is adapted to generate a first vessel model defining the position, shape and dimension of the first vessel, to generate a second vessel model defining a position, shape and dimension of the second vessel and to generate the vessel opening model based on the generated first vessel model and the generated second vessel model.

11. The navigation assistance system as defined in claim 1, wherein the graphical representation generation unit is adapted to generate the graphical representation in accordance with representation parameters defining how the implanted object opening model, the vessel opening model and the provided position of the interventional instrument are to be presented, wherein the representation parameters depend on the provided position of the interventional instrument.

12. An interventional system for performing an interventional procedure, the interventional system comprising:
an interventional instrument,
the navigation assistance system for assisting in navigating the interventional instrument as defined in claim 1.

13. A navigation assistance method for assisting in navigating an interventional instrument within a subject, the navigation assistance method comprising:
providing an interventional image data set showing an implanted object with an opening and a vessel with an opening by an interventional image data set providing unit,
providing the position of the interventional instrument by a position providing unit in a frame of reference,
generating an implanted object opening model and a vessel opening model based on the provided interventional image data set by a model generation unit, wherein the implanted object opening model defines the position, shape and dimension of the opening of the implanted object in the frame of reference and wherein the vessel opening model defines the position, shape and dimension of the opening of the vessel in the frame of reference, generating a graphical representation of the implanted object opening model, the vessel opening model and the provided position of the interventional instrument by a graphical representation generation unit.

\* \* \* \* \*